US009560977B2

(12) United States Patent
Cohen et al.

(10) Patent No.: US 9,560,977 B2
(45) Date of Patent: Feb. 7, 2017

(54) METHOD FOR ESTIMATING CHANGES OF CARDIOVASCULAR INDICES USING PERIPHEAL ARTERIAL BLOOD PRESSURE WAVEFORM

(71) Applicant: Massachusetts Institute of Technology, Cambridge, MA (US)

(72) Inventors: Richard Jonathan Cohen, Chestnut Hill, MA (US); Kichang Lee, Newton Highlands, MA (US); Tatsuya Arai, Franklin, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 57 days.

(21) Appl. No.: 14/315,741

(22) Filed: Jun. 26, 2014

(65) Prior Publication Data

US 2014/0358015 A1 Dec. 4, 2014

Related U.S. Application Data

(63) Continuation of application No. 12/563,469, filed on Sep. 21, 2009, now abandoned.

(51) Int. Cl.
*A61B 5/02* (2006.01)
*A61B 5/021* (2006.01)
*A61B 5/029* (2006.01)

(52) U.S. Cl.
CPC .............. *A61B 5/021* (2013.01); *A61B 5/029* (2013.01); *A61B 5/02028* (2013.01)

(58) Field of Classification Search
CPC ...... A61B 5/021; A61B 5/02028; A61B 5/029
See application file for complete search history.

(56) References Cited

U.S. PATENT DOCUMENTS

2008/0287812 A1* 11/2008 Parlikar et al. ............... 600/485

OTHER PUBLICATIONS

Kouchoukos et al. (Estimationof Stroke Volume in the Dog by a Pulse Contour Method, Cir. Res. vol. XXVI, May 1970, pp. 611-623).*
A. C. Guy and J. E. Hall, Textbook of Medical Physiology, 2000, 10th ed., Saunders, Philadelphia, US.

(Continued)

*Primary Examiner* — Michael Kahelin
*Assistant Examiner* — Tho Tran
(74) *Attorney, Agent, or Firm* — Sam Pasternack; MIT Technology Licensing Office

(57) ABSTRACT

The systems and methods described herein enable reliable estimation of cardiovascular indices on real-time, non-invasive or minimally-invasive, and beat-to-beat basis. Cardiovascular indices which can be estimated include: stroke volume (SV), which being limited to, cardiac output (CO) and total peripheral resistance (TPR). In various embodiments, one or more of these indices are estimated continuously, on a beat-to-beat basis, using peripheral arterial blood pressure (ABP) waveforms and certain parameters derived from the peripheral ABP waveforms. The derived parameters are substantially insensitive to distortions of the ABP waveform arising from tapered arterial branches throughout the arterial tree. The methods describe herein can provide a more accurate and reliable estimate of hemodynamic parameters than existing techniques.

27 Claims, 6 Drawing Sheets

(56) References Cited

OTHER PUBLICATIONS

H. Barcroft, O. G. Edholm, J. McMichael, and E. P. Sharpy-Schafer, "Posthaemorrhagic fainting. Study by cardiac output and forearm flow,", Lancet, 1944, pp. 489-491.
R. Mukkamala, A.T. Reisner, H. M. Jojman, R. G. Mark, and R. J. Cohen, "Continuous cardiac output monitoring by peripheral blood pressure waveform analysis," IEEE Trans Biomed Eng, 2006, pp. 459-467, vol. 53.
W. Ganz, R. Domonso, H. S. Marcus, J. S. Forrester, and H. J. Swan, A new technique for measurement of cardiac output by thermodilution in man, Am J. Cardiol, 1971, pp. 392-396, vol. 27.
R. D. Yoder and E. A. Swan, "Cardiac output comparison of Steward-Hamilton and gamma-function techniques," J Appl Physiol, 1971, pp. 318-321, vol. 31.
R.J. Levy, et al., "An evaluation of a noninvasive cardiac output measurement using partial carbon dioxide rebreathing in children," Anesth Analg, 2004, pp. 1642-1647, vol. 99.
M. Botero, et al., "Measurement of cardiac output before and after cardiopulmonary bypass: Comparison among aortic transit-time ultrasound, thermodilution, and noninvasive partial CO2 rebreating." J Cardiothorac Vasc Anesth, 2004, pp. 563-572, vol. 18.
M. J. Bourgeois, et al., "Continuous determination of beat to beat stroke volume from aortic pressure pulses in the dog," Circ Res, 1976, pp. 15-24, vol. 39.
G. Antonutto, M. Girardis, D. Tunize, and P.E. Di Prampero, "Noninvasive assessment of cardiac output from arterial pressure profiles during exercise," Eur J Appl Physiol Occup Physiol, 1995, pp. 18-24, vol. 72.
J. D. Redling and M. Akay, "Noninvasive cardiac output estimation: a preliminary study," Biol Cybern, 1997, pp. 111-122, vol. 77.
T. Nicminen, T. Koobi, and V. Turjanmas, "Can stroke volume and cardiac output be determine reliably in a tilt-table test using the pulse contour method?," Clin Physiol, 2000, pp. 488-495, vol. 20.
C. Cerutti, M. P. Guestin, P. Molino, and C. Z. Paultre, "Beat-to-beat stroke volume estimation from aortic, pressure waveform in conscious rats: comparison of models," Am J Physiol Heart Circ Physiol, 2002, pp. H1 148-155.
N. W. Linton and R. A. Linton, "Estimation of changes in cardiac output from the arterial blood pressure waveform in the upper limb," Br J Anaesth, 2001, pp. 486-496, vol. 86.
G. Antonutto, et al., "Assessment of cardiac output from noninvasive determination of arterial pressure profile in subjects at rest," Eur J Appl Physicol Occup Physiol, 1994, pp. 183-188. vol. 69.
W. J. Stok, R. C. Stringer, and J. M. Karemaker, "Noninvasive cardiac output measurement in orthostasis: pulse contour analysis compared with acetylene rebreathing," J Appl Physiol, 1999, pp. 2266-2273, vol. 87.
J. J. Van Lieshout and K. H. Wesseling, "Continuous cardiac output by pulse contour analysis?," Br J Anaesth, pp. 467-469, vol. 86.
D. Burkhoff, et al, "Assessment of Windkessel as a model of aortic input impedance," Am J Physiol, 1988, pp. H742-H753, vol. 255.
Z. Lu and R. Mukkamala, "Continuous cardiac output monitoring in humans by invasive and noninvasive peripheral blood pressure waveform analysis," J Appl Physiol, 2006, pp. 598-606, vol. 101.
P. Molino, et al., "Beat-to-beat estimation of Windkessel model parameters in conscious rats," Am J Physiol, 1998, pp. H171-H172, vol. 274.
J. A. Herd, N. R. Leclair, and W. Simon, "Arterial pressure pulse contours during hemorrhage in anesthetied dogs," J Appl Physiol, 1966, pp. 1864-1868, vol. 21.
M. W. Mohiuddin , G. A. Leine, and C. M. Quick, "Increase in pulse wavelength causes the systemic arterial tree to degenerate into a classical Windkessel," Am J Physiol Heart Circ Physiol, 2007, pp. H1164-H1171, vol. 293.
J. M. Bland and D. G. Altman, "Statistical methods for assessing agreement between two methods of clinical measurement," Lancet, 1986, pp. 307-310, vol. 1.
K. Dewitte, et all., "Application of the Bland-Altman plot for interpretation of method-comparison studies: a critical investigation of its practice," 2002, Clin Chem, pp. 799-801, vol. 48.
X. Xiao, et al., "Bed rest effects on human calf hemodynamics and orthostatic intolerance: a model-based analysis," Aviat Space Environ Med, 2005, pp. 1037-1045, vol. 76.
K. H. Wesseling, et al., "A simple device for the continuous measurement of cardiac output. Its model basis and experimental verification.," Adv Cardiovasc Phys, 1983, pp. 16-52, vol. 5.
K. H. Westeling, et al., "Computation of aortic flow from pressure in humans using a nonlinear, three-element model," J Appl. Physiol, 1993, pp. 2566-2573, vol. 74.
J. Sugawars, et al., "Non-invasive assessment of cardiac output during exercise in healthy young humans: comparison between Modelflow method and Doppler echocardiography method," Acta Physiol Scand, 2003, pp. 361-366, vol. 179.
E. Tam, et al., "Correction of cardiac output obtained by Modelflow from finger pulse pressure profiles with a respiratory method in humans," Clin Sci (Lond), 2004, pp. 371-376, vol. 106.
J. J. Remmen, et al., "Finapres arterial pulse wave analysis with Modelflow is not a reliable non-invasive method for assessment of cardiac output" Clin Sci (Lond), 2002, pp. 143-149, vol. 103.
T. Nakamura, et al., "[Evaluation of continuous blood pressure monitoring by arterial tonometry in the aged]," Masul, 1997, pp. 1618-1624, vol. 46.
R. A. Nelesen and J. E. Dimsdale, "Use of radial arterial tonometric continuous blood pressure measurement in cardiovascular reactivity studies," Blood Press Monit, 2002, pp. 259-263, vol. 7.

* cited by examiner

METHOD FOR ESTIMATING CHANGES OF CARDIOVASCULAR INDICES USING PERIPHEAL ARTERIAL BLOOD PRESSURE WAVEFORM

This application is a continuation of U.S. patent application Ser. No. 12/563,469 filed on Sep. 21, 2009 and claims priority to U.S. Provisional Application No. 61/098,906 filed on Sep. 22, 2008, both of which are incorporated herein by reference.

FIELD OF THE INVENTION

The present invention relates to systems and methods for determining cardiovascular indices from peripheral arterial blood pressure.

BACKGROUND

Cardiac output (CO), stroke volume (SV), and total peripheral resistance (TPR) are among important hemodynamic parameters to be monitored and assessed in critically ill patients, ambulatory patients, as well as patients undergoing surgical procedures. CO and SV are valuable indicators of mechanical/pathological/physiological status of a subject's heart. TPR is a measure of a subject's vascoconstriction ability associated with certain pathophysiological conditions. Several techniques have been developed to measure or estimate one or more of these hemodynamic parameters. (See for example R. Mukkamala et al., "Continuous cardiac output monitoring by peripheral blood pressure waveform analysis," *IEEE Trans Biomed Eng*, vol. 53, pp. 459-67, Market 2006; W. Ganz et al., "A new technique for measurement of cardiac output by thermodilution in man," *Am J Cardiol*, vol. 27, pp. 392-6, April 1971; M. J. Bourgeois et al., "Continuous determination of beat to beat stroke volume from aortic pressure pulses in the dog," *Circ Research*, vol. 39, pp. 15-24, July 1976.) Estimation of cardiovascular indices on real-time, non-invasive or minimally-invasive, and beat-to-beat basis would be a useful diagnostic tool for clinical and scientific applications, e.g., in hospital stings for patient care or research settings for determining the efficacy of certain medications.

SUMMARY

Systems and methods are described for estimating the stroke volume (SV) of a cardiac cycle of the heart and other related cardiovascular indices of a subject using parameters derived from the arterial blood pressure waveform which are substantially insensitive to distortions arising from the propagation of the arterial pulse through the arterial tree. In certain embodiments, stroke volume (SV) is estimated from parameters derived from the arterial pressure waveform such as the end-diastolic blood pressure, mean arterial pressure, duration of the cardiac cycle, and a measure of the duration of systole (e.g., the interval from the onset of systole to the peak of the arterial blood pressure waveform). Because these parameters are substantially insensitive to distortions resulting from the propagation of the arterial pulse through the arterial tree, the systems and the methods described herein can provide more reliable and accurate estimates of the stroke volume and related cardiovascular indices than can existing techniques. Additionally, the systems and methods of the present invention have an advantage in that estimates of the cardiovascular indices can be provided on a real-time, non- or minimally-invasive, beat-to-beat basis, e.g., the blood pressure values can be obtained from peripheral arterial blood-pressure waveforms and processed to provide the estimates.

In various embodiments, a system for estimating stroke volume on a beat-to-beat basis comprises a means of recording the arterial blood pressure signal, a means of processing the arterial blood pressure signal to obtain a plurality of parameters which are substantially insensitive to distortions arising from the propagation of the arterial pulse through the arterial tree, and a means of incorporating the parameters into a formula or algorithm to estimate the stoke volume of the heart. From the stroke volume one may further estimate cardiovascular indices such as cardiac output and peripheral vascular resistant.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate amending of the invention. In the drawings, like reference characters generally refer to the features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

DETAILED DESCRIPTION

I. Introduction

The systems and methods described herein enable reliable estimation of cardiovascular indices on real-time, non-invasive or minimally-invasive, and beat-to-beat basis. In certain embodiments, the invention provides a useful diagnostic tool for clinical and scientific applications, e.g., in hospital settings for patient care or research settings for determining the efficacy of certain medications. Cardiovascular indices which can be estimated include, without being limited to, stroke volume (SV, the volume of blood ejected by the ventricles during the systolic phase), cardiac output (CO, the average volume of blood pumped into the aorta by the heart per unit time), and total peripheral resistance. (TPR, the sum of the resistance of all peripheral vasculature in the systemic circulation). In various embodiments, one or more of these indices are estimated continuously, on a beat-to-beat basis, using peripheral arterial blood pressure (ABP) waveforms for each cardiac cycle. Unlike existing techniques, the systems and methods described herein utilize parameters derived from the ABP waveforms which are substantially insensitive to distortions of the ABP waveforms arising from the propagation of the arterial pulse through the tapered arterial branches throughout the arterial tree.

Figure 1:
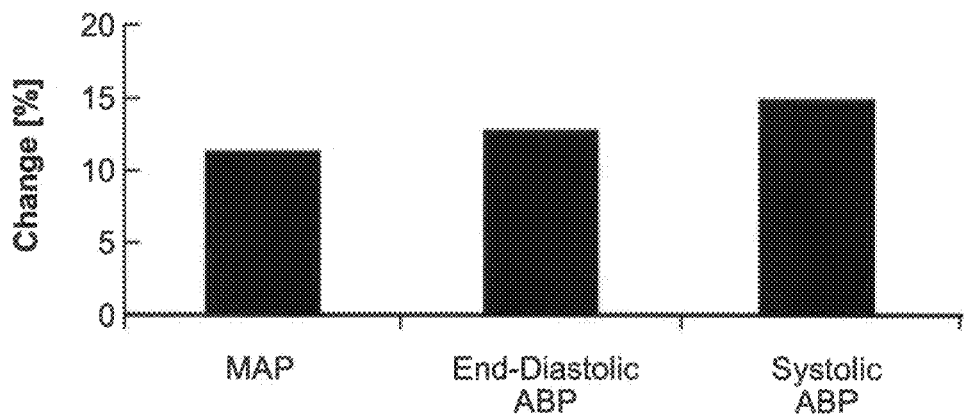
FIG. 1 depicts the changes in parameters derived from the arterial blood pressure waveform when recorded in a peripheral versus central location in the arterial tree.

FIG. 1 shows the changes in the ABP values that occurred from central to radial artery in swine. The change [%] is defined as $$\frac{P_{Central} - P_{radial}}{P_{Central}} \times 100 [\%]$$

where $P_{central}$ and $P_{radial}$ represent central and radial ABP values, respectively. As can be seen, the systolic ABP has the largest standard deviations. One the other hand, MAP and end-diastolic ABP values showed smaller standard deviations. These ABP values can provide a more accurate and reliable estimate of actual hemodynamic parameters.

CO, SV, and TPR represent important hemodynamic parameters monitored and assessed in ambulatory and critically ill patients. Currently, hemodynamic monitoring of patients in critical care setting depends heavily on monitoring ABP because of its easier accessibility compared to CO, SV, and TPR. However, ABP can be a late indicator of hemodynamic abnormality, e.g., internal bleeding or hemorrhage, because physiologic feedback systems maintain ABP to prevent development of hemodynamic collapse and death. CO and SV are, on the other hand, a direct measure that enables earlier prediction of hemodynamic collapse, but they are difficult to obtain. TPR can be an important parameter to monitor, because low TPR is believed to be an indicator of orthostatic intolerance, or orthostatic hypotension. In certain embodiments, one or more of CO, SV, and TPR are estimated from peripheral ABP waveforms using the systems and methods described herein.

II. Existing Techniques

There currently exist several techniques for estimating cardiac output. However, these techniques involve systolic ABP information, which is susceptible to distortion due to tapered arterial branches throughout the arterial tree.

The most accurate method for measuring CO involves placing an ultrasonic flow probe around the aorta. However, this method requires a drastic procedure of opening the chest. The most commonly used clinical method for the measurement of CO is thermodilution. This method involves injecting cold saline through a central vein catheter and measuring temperature change in the pulmonary artery. Then, CO is calculated using the Stewart-Hamilton equation. (See A. Swan, "Cardiac output: comparison of Stewart-Hamilton and gamma-function techniques," *J Appl Physiol*, vol. 31, pp. 318-21, August 1971.) However, thermodilution requires a pulmonary artery catheterization, which is associated with cardiovascular risks, especially for infants and children. Also, this method is reported to have limited accuracy. Boreto et al. compared a continuous thermodilution method with an ultrasonic flow probe and reported 0.36 L/min bias and 1.96 L/min of standard deviation (SD). (See M. Boreto et al., "Measurement of cardiac output before and after cardiopulmonary bypass: Comparison among aortic transmit-time ultrasound, thermodilution, and noninvasive partial $CO_2$ rebreathing," *J Cardiothorac Vasc Anest*, vol. 18, pp. 563-72. October 2004.)

The pulse contour method (PCM), which continuously calculated CO based on mathematical analysis of peripheral ABP waveform, has been extensively studied for minimally (or non)-invasive CO measurement. The method generally calculates stroke volume (SV), the volume of blood ejected by the ventricles during systolic phase, by analysis of area under systolic ABP curve over aortic impedance [9]. (See G. Antonutto, et al., "Noninvasive assessment of cardiac output from arterial pressure profiles during exercise," *Eur J Application Physiol Occup Physiol*, vol. 72, pp. 18-24, 1995.) However, since PCM generally determines proportional CO within a scaling faction of impedance, PCM requires calibration with another CO measurement technique for absolute CO measurements. Also, PCM has not achieved sufficient accuracy or reliability to have been adopted clinically.

Figure 2A:
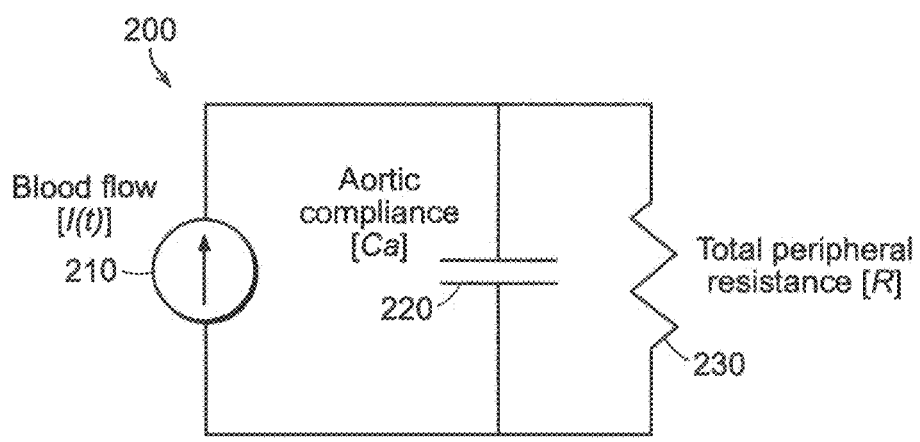
FIG. 2A-2C depicts aspects of a Windkessel cardiovascular model.

Another approach to less-invasively estimated CO is based on the Windkessel model, which is a widely accepted model for the cardiovascular system. (See for example R. Mukkamala et al., "Continuous cardiac output monitoring by peripheral blood pressure waveform analysis," *IEEE Transportation Biomed Eng*, vol. 53, pp. 459-67, March 2006; and D. Burkhoff et al., "Assessment of Windkessel as a model of aortic input impedance," *Am J Physiol*, vol. 255, pp. H742-53, October 1988.) In this model the heart and arterial tree are modeled with an equivalent electrical circuit 200 as depicted in FIG. 2A. The heart, total peripheral resistance (TPR), and aortic compliance ($C_a$) are modeled as a current source 210, resistance 230, and capacitance 220, respectively. Current (blood flow, BF) and voltage (arterial blood pressure, ABP) averaged over multiple beats represent CO and mean arterial pressure (MAP), respectively. From FIG. 2A, the instantaneous blood flow can be described by:

$$BF(t) = \frac{ABP(t)}{TPR} + C_a \times \frac{d}{dt} ABP(t) \quad (1)$$

where, BF(t) is instantaneous blood flow. In the Windkessel model, the blood flow is taken as a series of impulses as depicted in FIG. 2C, which drive the two-parameter system. From EQ. 1, the characteristic time constant τ is defined as $$\tau = TPR \times C_a \quad (2)$$

Figure 2B:
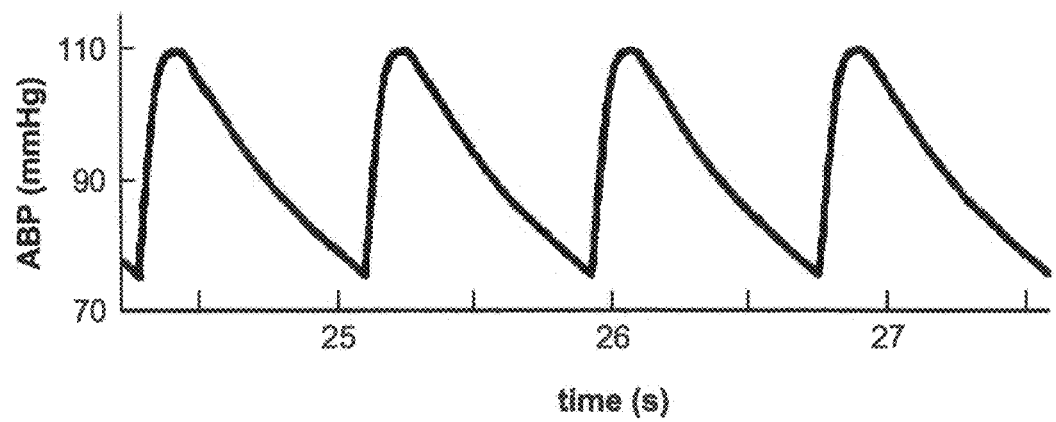
Figure 2C:
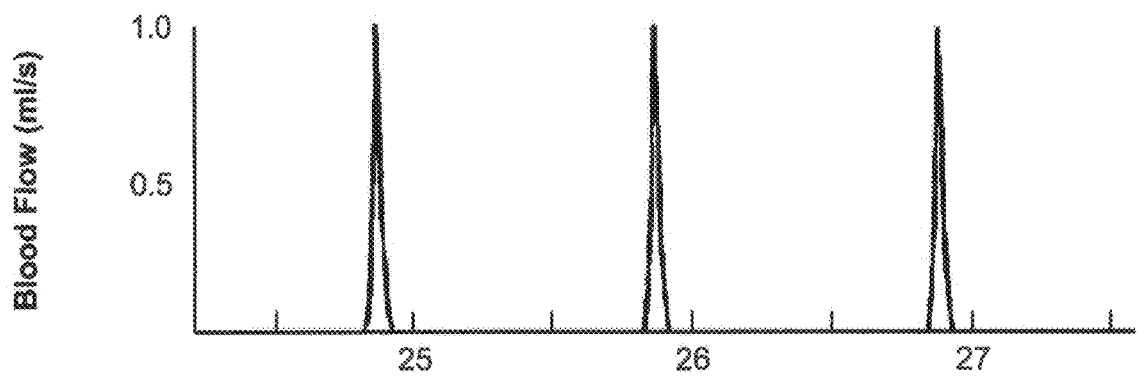

The characteristic time constant characterizes the exponential decay of the arterial blood pressure, as depicted in FIG. 2B. Averaging EQ. 1 yields:

$$MAP = CO \times TPR \quad (3)$$

Combining EQS. 2-3 and rearranging terms gives the following results.

$$CO = \frac{MAP}{TPR} \quad (4)$$

$$CO \propto \frac{MAP}{\tau}$$

In this model, linearity of the system and an exponential decay during diastolic phase are assumed. However, it is common that peripheral ABP waveforms distort as they propagate through the elastic tapered arterial network. Since ABP waveforms measured in peripheral arterial vessels generally do not have exponentially decaying property during diastolic phase, it is difficult to obtain the characteristic time constant $\tau$. (See R. Mukkamala, et al., "Continuous cardiac output monitoring by peripheral blood pressure waveform analysis," *IEEE Trans Biomed Eng*, vol. 53, pp. 459-67, Market 2006.)

As opposed to the PCM which analyzes individual ABP waveforms, Mukkamala et al. used an auto-regressive moving average (ARMA) model for $\tau$ estimation over a time scale of six minutes. The technique utilizes a PPt impulse train as the input and the ABP waveform as the output signal for the ARMA analysis. The system impulse response function is estimated using six minute segments of peripheral ABP data. The characteristic time constant $\tau$ is estimated by fitting the impulse response function for a selected time interval of a measured decaying exponential. Then, proportional CO is calculated using EQ. 4. Analyzing data from five Yorkshire swine, Mukkamala et al. achieved an overall CO root-mean square normalized error (RMSNE) of 14.6%.

A common feature of all aforementioned existing techniques is use of systolic and diastolic ABP information. However, systolic ABP information is susceptible to distortions caused by propagation through the elastic, tapered arterial network. Inclusion of distorted systolic blood pressure (SBP) information can lead to error-prone hemodynamic parameters.

III. Estimating Cardiovascular Indices

Systems and methods of the present invention have been developed to estimate cardiovascular indices based on end-diastolic blood pressure (end-DBP) values, beat-average arterial pressures (MAP), beat duration, and the time interval from the onset of systolic blood pressure (SBP) to peak SBP in a peripheral ABP waveform (duration of systole). These values can be used in an algorithm to estimate one or more hemodynamic parameters, e.g., CO, SV, and TPR, an a beat-to-beat basis. The methods utilize a Windkessel model of the cardiac system. The calculation process involves obtaining the characteristic time constant $\tau$ that governs exponential decay during diastole. The characteristic time constant $\tau$ can be used with the insensitive ABP values to distortion to calculate proportional CO, SV, and TPR based on the Windkessel model. These values used for estimating hemodynamic parameters were selected because they are relatively insensitive to the distortion of the ABP waveform in the arterial tree. Therefore, the linear assumption in the Windkessel model holds, and reliable estimates of the hemodynamic parameters can be obtained.

Figure 3A:
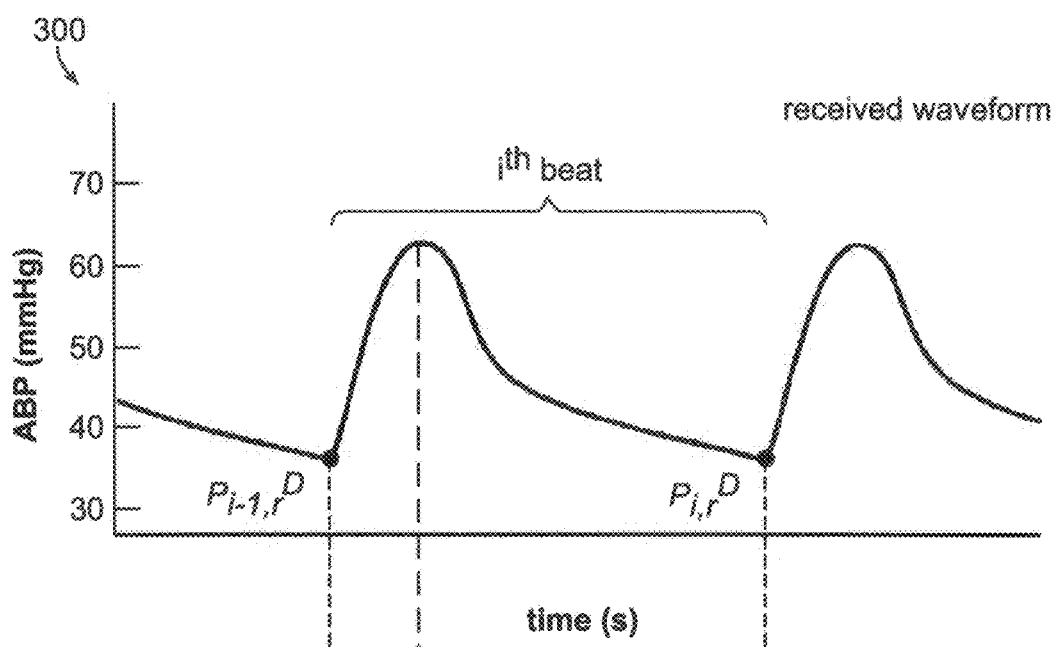
FIG. 3A depicts about two cardiac cycles of a peripheral arterial blood pressure waveform.
Figure 3B:
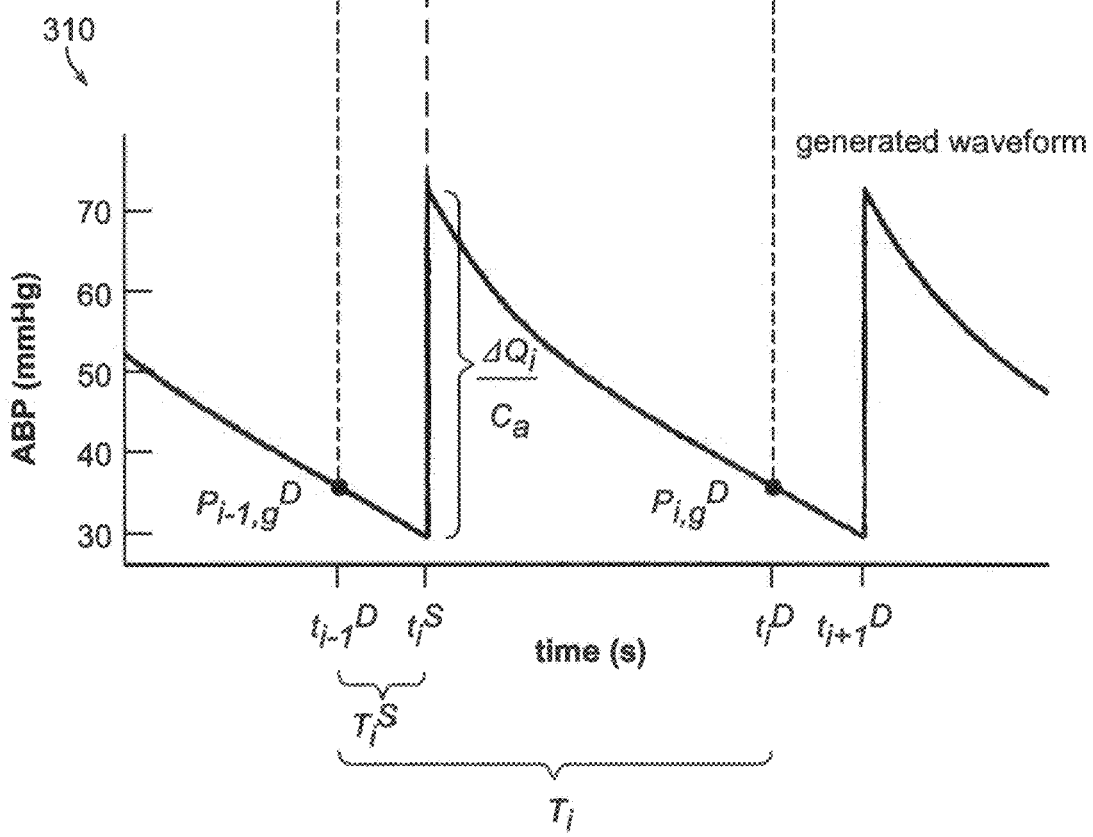
FIG. 3B depicts an embodiment of a numerically generated arterial blood pressure waveform used to estimate cardiovascular indices.

For heuristic purposes, FIGS. 3A-3B illustrate certain concepts employed in an embodiment of a method for estimating cardiovascular indices. In this approach, a peripheral ABP waveform 300 as depicted in FIG. 3A is received from a subject. A pressure transducer and associated electronic equipment can be used to provide the peripheral ABP waveform 300. A second waveform 310 is numerically generated as depicted in FIG. 3B based on the Windkessel model. In the figures, P denotes ABP, and the superscripts S and D denote systolic and diastolic points, respectively. $\Delta Q_i$ denotes the stroke volume (SV) of the $i^{th}$ beat. Continuing with this embodiment, $C_a$ is assumed to be constant for each subject, and each impulse of the generated ABP waveform is substantially aligned to each systolic peak point of the received peripheral ABP. The functional form of the generated ABP waveform can be described by the following equations for the $i^{th}$ cardiac cycle.

$$P(t) = P_{i-1,g}^D \exp\left[\frac{-(t - t_{i-1}^D)}{\tau_i}\right] \text{ for } t_{i-1}^D < t < t_i^S \quad (5A)$$

$$P(t) = \left[P_{i-1,g}^D \exp\left(\frac{-T_i^S}{\tau_i}\right) + \frac{\Delta Q_i}{C_a}\right] \exp\left[\frac{-(t - t_i^S)}{\tau_i}\right] \text{ for } t_i^S < t < t_i^D \quad (5B)$$

where $t_{i-1}^D$ and $t_i^S$ are time stamps of the end of diastole (onset of systole) and the peak systolic point of the $i-1^{th}$ and $i^{th}$ beat ABP waveform, respectively. $\tau_i$ represents the characteristic time constant of the cardiac cycle, $P_{i,r}^D$ represents the end-DBP value in the $i^{th}$ beat of the received ABP waveform, and $P_{i,g}^D$ represents the end-DBP value in the $i^{th}$ beat of the generated ABP waveform. In this embodiment and referring to FIGS. 3A-3B, the end-DBP values of the generated waveform are set equal to the end-DBP values of the received waveform, e.g., $P_{i,g}^D = P_{i,r}^D$, $T_i^S$ and $T_i$ represent the periods or time duration of systole and beat duration of the ABP waveform, respectively.

Equations 5A and 5B can be used to obtain an average of ABP over the $i^{th}$ beat for the generated ABP waveform 310. The mean arterial pressure for the $i^{th}$ beat of the generated waveform ($MAP_{i,g}$) can be expressed in terms of $T_i$, $P_{i-1,g}^D$, $P_{i,g}^D$, $\Delta Q_i$, and $C_a$ as follows.

$$MAP_{i,g} = \frac{1}{T_i} \int_{t_i^D}^{t_{i+1}^D} P_{i,g}(t) dt = \frac{\tau_i}{T_i}\left(P_{i-1,g}^D + \frac{\Delta Q_i}{C_a} - P_{i,g}^D\right) \quad (6)$$

Referring to FIG. 3B, the $i^{th}$ beat pulse pressure (PP) of the generated ABP waveform can be calculated by subtracting values of the two points at $t_i^S$ of the two exponential curves given by EQS. 5A-5B:

$$\frac{\Delta Q_i}{C_a} = P_{i,g}^D \exp\left[\frac{(T_i - T_i^S)}{\tau_i}\right] - P_{i-1,g}^D \exp\left[\frac{-T_i^S}{\tau_i}\right] \quad (7)$$

Substituting EQ. 6 into EQ. 7 yields:

$$MAP_{i,g} = \frac{\tau_i}{T_i}\left\{P_{i,g}^D\left(\exp\left[\frac{(T_i - T_i^S)}{\tau_i}\right] - 1\right) + P_{i-1,g}^D\left(1 - \exp\left[\frac{-T_i^S}{\tau_i}\right]\right)\right\} \quad (8)$$

In various embodiments, the received ABP waveform 300 over the $i^{th}$ mean arterial pressure ($MAP_{i,r}$). The values for $T_i$, $T_i^S$, $P_{i-1,g}^D$, and $P_{i,g}^D$ can be set equal to the corresponding values determined from the received ABP waveform. The value ($MAP_{i,g}$) can be set equal to ($MAP_{i,r}$) and EQ. 8 can be numerically solved to obtain a value for $\tau_i$. The obtained value $\tau_i$ can be used to estimate proportional CO using EQ. 4. In some embodiments, the value $\tau_i$ can be used to estimate proportional SV and/or TPR An advantage of the method described above is that $\tau_i$ is calculated from the end-DBP, the time interval from the current end-DBP to the next end-DBP (beat duration), the time interval from the preceding end-DBP to peak systole (the duration of Systole), and current MAP. Information from the systolic blood pressure waveform, which is less reliable than end-DBP due to distortion, is not directly used. Moreover, the method described above can estimate $\tau_i$ on a beat-to-beat basis while other existing techniques can require data from multiple cardiac cycles and include multiple data processing steps. As an example, the ARMA model requires multi-steps to obtain $\tau$ (auto regressive (AR) and moving average (MA) parameter determination, and iteration to generate an impulse response, see M. J. Bourgeois et al., "Continuous determination of beat to beat stroke volume from aortic pressure pulses in the dog," *Cir Res*, vol. 39, pp. 15-24, July 1976; and G. Antonutto et al., "Noninvasive assessment of cardiac output from arterial pressure profiles during exercise," *Eur J Application Physiol Occup Physiol*, vol. 72, pp. 18-24, 1995.) For a practical use, taking medians of $\tau_i$ and $T_i^S$ in EQ. 8 over about 33 beats can exclude outliers. The number of 33 was empirically found by the inventors to provide the smallest estimation errors under a variety of conditions.

The use of end-DBP and MAP has corroboration in results reported by Herd et al. (See J. A. Herd et al., "Arterial pressure pulse contours during hemorrhage in anesthetized dogs," *J Appl Physiol*, vol. 21, pp. 1864-8, November 1966.) In this work, it was shown that pulse pressure calculated as difference of MAP and DBP, as opposed to difference of SBP and DBP, had better correlation with measured CO.

Figure 4:
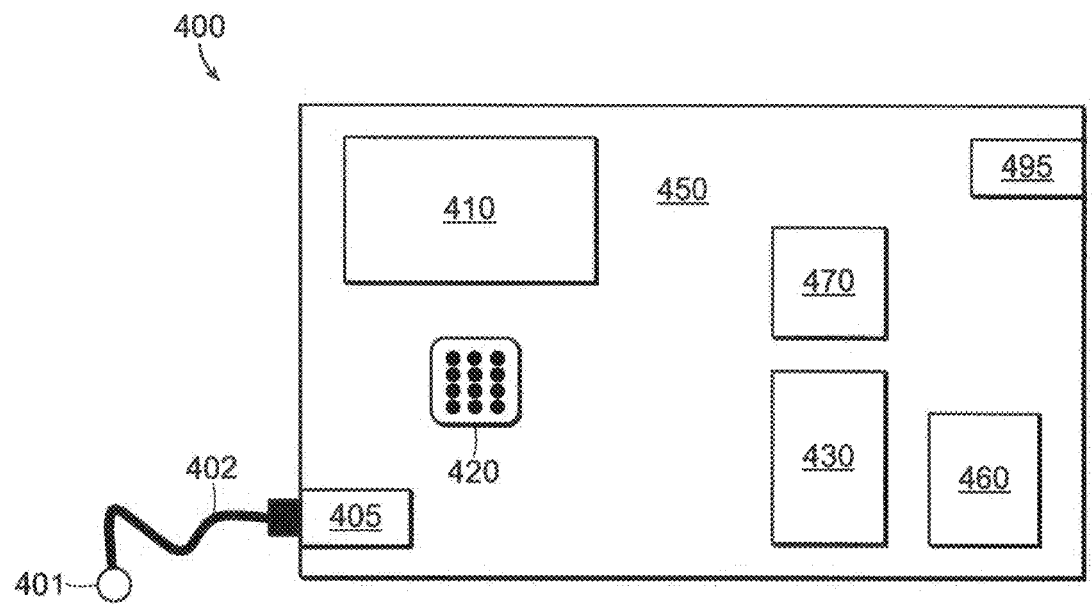
FIG. 4 represents an embodiment of a system for estimating a cardiovascular index.
Figure 5A:
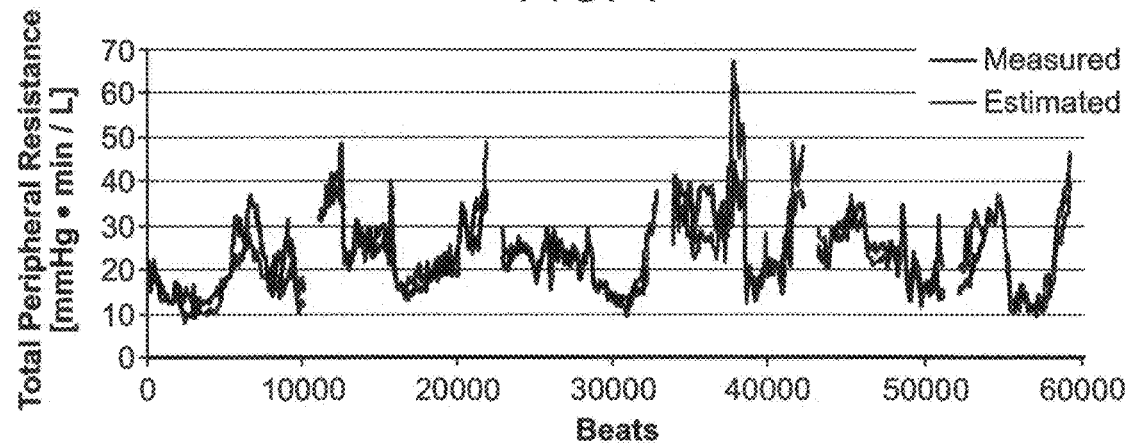
FIG. 5A represents plots of estimated and measured total peripheral resistance (TPR) for six trials.
Figure 5B:
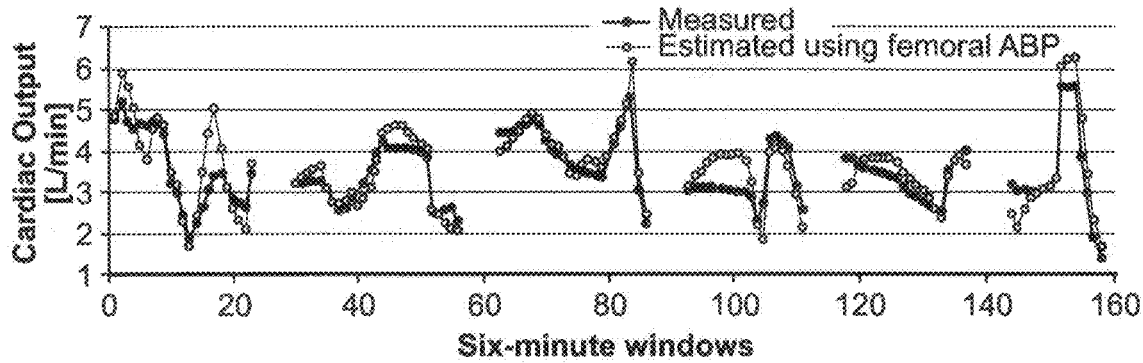
FIG. 5B represents plots of estimated and measured cardiac output (CO) for six trials using femoral ABP.
Figure 5C:
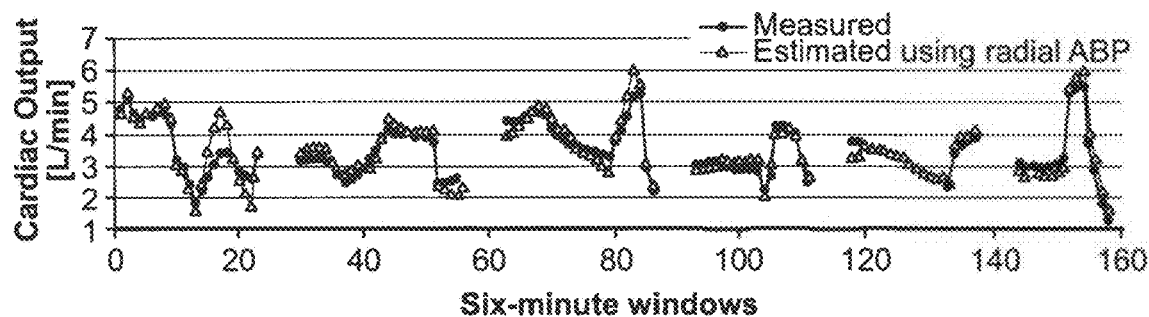
FIG. 5C represents plots of estimated and measured cardiac output (CO) for six trials using radial ABP.
Figure 5D:
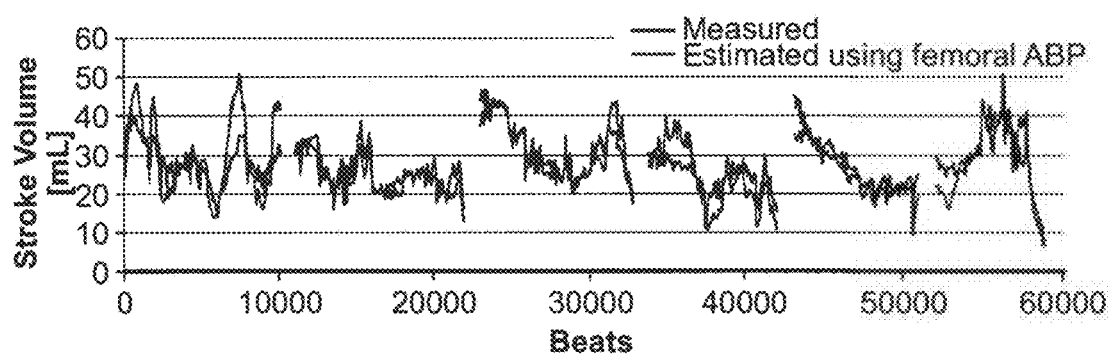
FIG. 5D represents plots of estimated and measured stroke volume (SV) for six trials using femoral ABP.
Figure 5E:
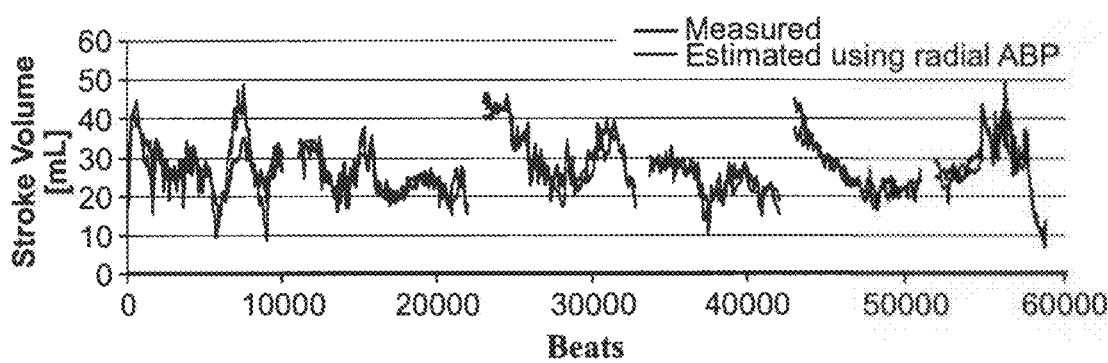
FIG. 5E represents plots of estimated and measured stroke volume (SV) for six trials using radial ABP.

An embodiment of a system 400 for estimating cardiovascular indices is shown in FIG. 4. In certain embodiments, the system 400 comprises a sensor 401 in communication with an index estimation instrument 450. The sensor 401 can be disposed on a subject and adapted to generate an electrical signal in response to peripheral arterial blood pressure of the subject. The sensor can provide the signal to the instrument 450 for processing. In various embodiments, the electrical signal is representative of a peripheral ABP waveform of the subject. The sensor 401 can provide the signal to the instrument via an electrical or optical link 402, e.g., a shielded electrical cable or fiber-optic cable. In some embodiments, the sensor provides the electrical signal to the instrument 450 via a wireless link an RF, ultrasonic, or optical communication link.

In various embodiments, the index estimation instrument 450 comprises a data intake port 405, a processor 430, and a memory 440. In certain embodiments, the instrument 450 further comprises a video display 410, a user-interface device 420, and a communication port 495.

The data intake port 405 can comprise a data acquisition module, e.g., a USB-based, ethernet-based, GPIB-based, RS-232 or RS-435, data acquisition device. The data intake port 405 can be configured as a receive-only port or as a transceiving port, e.g., capable of receiving data from sensor 401 and transmitting instructions to the sensor. In operation the data intake port 405 receives data representative of an ABP waveform from the sensor 401 and forwards the data to the central processor 430 or memory 460.

In certain embodiments, the processor 430 comprises hardware, software, or a combination thereof adapted to process the signal received from the sensor 401. In various embodiments, waveform processor 430 records data values as a function of time for the received signal. The waveform processor can further determine values associated with the received ABP signal. As an example, waveform processor can determine the duration of a cardiac-cycle $\tau_i$, mean arterial pressure of a cardiac cycle $MAP_i$, end-DBP values $t_i^D$, $P_i^D$, time of peak systolic value $t_i^3$, and duration to peak systolic value $T_i^S$.

Memory 460 can comprise any type of combination of memory components. Included within some embodiments of the index estimation instrument 450 is each of main memory unit 460 and cache memory (not shown separately). The cache memory and main memory 460 can be any one of the following types of memory: static random access memory (SRAM), dynamic random access memory (DRAM), ferroelectric RAM (FRAM), or various enhanced versions thereof known to those skilled in the art of memory devices, e.g., burst SRAM or synchburst SRAM (BSRAM), enhanced DRAM (EDRAM), double data rate SDRAM (DDR SDRAM). In some embodiments, memory 460 can comprise or include an external device, e.g., a USB memory stick or remote memory device in communication with the instrument 450 through communication port 495.

The processing unit 470 can comprise any one of the following component configurations: logic circuits that respond to and process instructions provided from the main memory unit 360; a microprocessor unit, such as: those manufactured by Intel Corporation; those manufactured by Motorola Corporation; those manufactured by Transmeta Corporation of Santa Clara, Calif.; the RS/6000 processor such as those manufactured by International Business Machines; a processor such as those manufactured by Advanced Micro Devices; or any other combination of logic circuits capable of executing the system and methods described herein. Still other embodiments of the processing unit 470 include any combination of the following: a microprocessor, a microcontroller, a central processing unit with a single processing core, or a central processing unit with multiple processing cores. In various embodiments, processor 470 manages dataflow, data processing and operation of the index estimation instrument 450.

Communication port 495 can comprise any of a wide variety of network interface devices currently available. In various embodiments, communication port 495 provides an interface to a Local Area Network (LANGUAGE), Wide Area Network (WAN) or the world-wide Internet through any of a variety of connections including, but not limited to, standard telephone lines. LANGUAGE or WAN links (e.g., 802.1, T1, T3, 56 kb, X.25, SNA, DECNET), broadband connections (e.g., ISDN, Frame Relay, ATM, Gigabit Ethernet, Ethernet-over SONET), wireless connections, or some combination of any or all of the above. Connections can also be established using any of a variety of communication protocols (e.g., TCP/IP, IPX, SPX, NetBIOS, Ethernet, ARCNET, SONET, SDH, Fiber Distributed Data Interface (FDDI), RS232, RS485, IEEE 801.11, IEEE 802.11a, IEEE 802.11g, CDMA, GSM, WiMax and direct asynchronous connections). In some embodiments, the communication port 495 supports Secure Socket Layer (SSL) or Transport Layer Security (TLS) protocols. The communication port 495 can comprise any one of: a built-in network adapter; a network interface card; a PCMCIA network card; a card business network adapter; a wireless network adapter; a USB network adapter; a modem; or any other device suitable for interfacing the index estimation instrument 450 to a network.

User interface components can be integrated with the index estimation instrument 450. For example, a video display 410 can be included to visually display plots of received ABP waveforms and generated waveforms. The display 410 can also be used to post real-time values of estimated cardiovascular indices, and signal warnings [if?] life-threatening changes in a cardiovascular index are detected. A user-interface device 420 can also be integrated with the instrument, in the form of a keypad or touchpad integrated with the display 410, to provide for data entry by a system user. In some embodiments, the user-interface device 420 can be provided separately, e.g., a mouse, a keyboard, or a remote control device.

The aforementioned method to calculate SV can be rephrased by calculating SV from the five cardiovascular values that are substantially insensitive to distortion:

$$SV_{prop1}(i) = \frac{\Delta Q_i}{C_a} = f(MAP_i, P_i^D, P_{i+1}^D, T_i, T_i^S) \quad (9A)$$

Using the above five parameters, three independent dimensionless variables ($T_i^S/T_i$, $P_i^D/MAP_i$, and $P_{i-1}^D/MAP_i$), can be derived. One of the methods to calculate SV from the variables is to use linear regression to find coefficients for the variables. However, the physiological relationship among the three variables are not apparent. A formula or algorithm lets the three proportional SV estimates from different Windkessel models, $SV_{prop1}$, $SV_{prop2}$ and $SV_{prop3}$, rather than $T_i^S/T_i$, $P_i^D/MAP_i$, and $P_{i-1}^D/MAP_i$, represent the three independent variables. In this manner, without a loss of generality, we can construct SV estimates using three independent variables.

$$SV_{prop2}(i) = SV_{prop1}|_{T_i^S=0} = f(MAP_i, P_i^D, P_{i-1}^D, T_i) \quad (9b)$$

$$SV_{prop3}(i) = SV_{prop2}|_{P_i^D=P_{i-1}^D} = f(MAP_i, P_{i-1}^D, T_i) \quad (9c)$$

The second estimate $SV_{prop2}$ (9b) is regarded as the first model with $T_i^S=0$, and the third estimate $SV_{prop3}$ (9C) as the second model with $P_i^D=P_{i-1}^D$. Thus, the three independent variables can be converted into three independent SV. The final SV estimate of the $i_{th}$ beat will be, for example:

$$SV_i = C_a SV_{prop1}(i) \cdot \left(\frac{SV_{prop2}(i)}{SV_{prop1}(i)}\right)^{a_1} \cdot \left(\frac{SV_{prop3}(i)}{SB_{prop1}(i)}\right)^{a_2} \quad (10)$$

Note that EQ. 10 is a hybrid model of $SV_{prop1}$, $SV_{prop2}$ and $SV_{prop3}$ weighted by the coefficients $a_1$ and $a_2$. For example, if $a_1=0$ and $a_2=1$, then $SV=C_a SV_2$ and EQ. 9b is adopted. The coefficients allow non-discrete switching between the three models. By taking logarithm of EQ. 10, the equation becomes linear.

$$y(i,j) = D(j) + y_1(i,j) + a_1 X_1(i,j) + a_2 X_2(i,j) \quad (11)$$

where, i is beat number, j is subject matter, $y=\log(SV_i)$, $D(j)=\log(C_a)$, $y_1=\log(SV_{prop1})$, $X_1=\log(SV_{prop1}/SV_{prop0})$, and $X=\log(SV_{prop2}/SV_{prop1})$. Linear regression and least mean square error analysis give aortic compliances $C_a(j)$, $a_1$, and $a_2$. The coefficients $a_1$, and $a_2$ are common among all the subjects, and each compliance $C_a(j)$ is unique to the subject j.

Although EQ. 11 is a first order equation, it is possible to increase the order by introducing $X_1$ and $X_2$ to the higher power. EQ. 11 can be generalized as $$y(i,j) = D(j) + y_0(i,j) + \sum_{M=1}^{Mmax} \sum_{q=0}^{M} {}_M C_q \cdot a_{Mq} \cdot (X_1(i,j))^{M-q} (X_2(i,j))^q \quad (12)$$

where, M is the model order, ${}_M C_q$ is the combination of q items (disregarding order) from a collection of M items, while $a_{Mq}$ are the coefficients to be found by the linear regression analysis. Once the parameters are obtained, SV is calculated as $$SV = \exp(y) \quad (13)$$

CO is calculated by averaging SV over a period of time.

In certain embodiments, it requires a training data set to find the coefficients $a_{Mq}$. For that purpose, independently measured SV values or a plurality of CO and heart rate can be used.

In one preferred embodiment, the stroke volume of a cardiac cycle of a heart is estimated by first recording an arterial blood pressure signal, then processing the arterial blood pressure signal to obtain a plurality of parameters which are insensitive to distortion resulting from the propagation of the arterial pulse through the arterial tree, and then incorporating the parameters into a formula or algorithm (such as those described above) to estimate the stroke volume of the cardiac cycle of the heart.

In another preferred embodiment, the derived parameters include one or more of the following: mean arterial pressure of the cardiac cycle, end-diastolic pressure of the cardiac cycle, end-diastolic pressure of the immediately preceding cardiac cycle, duration of the cardiac cycle, duration of systole of the cardiac cycle.

In another preferred embodiment, the above method for estimating the stroke volume of a cardiac cycle is repeated for a plurality of cardiac cycles of the heart.

In another preferred embodiment the formula or algorithm employed incorporates a mathematical model of the arterial blood pressure signal.

In other preferred embodiment, the model is a Windkessel type model.

In another preferred embodiment the formula or algorithm incorporates one or more means of fitting the arterial blood pressure signal to one or more models.

In another preferred embodiment the formula or algorithm incorporates one or more means of fitting the arterial blood pressure signal to Windkessel type model.

In another preferred embodiment the formula or algorithm takes into account the number of dimensionless parameters that can be derived from the parameters that are derived from the arterial blood pressure waveform.

In other preferred embodiment the characteristic time constant of the cardiac cycle is estimated.

In another preferred embodiment the time constant associated with the cardiac cycle is estimated from time constants estimated for a plurality of cardiac cycles preceding and/or following the cardiac cycle.

In another preferred embodiment further the cardiac output is estimated. This may be accomplished for example by summing the stroke volumes of all the cardiac cycles within a time period and then dividing the duration of the time period.

In another preferred embodiment the total peripheral vascular resistance is estimated. This may be accomplished for example by computing the mean arterial pressure over a period of time and then dividing this quantity by the mean cardiac output over that same period of time.

In another preferred embodiment the arterial pressure signal is obtained from an intra-arterial measurement location.

In another preferred embodiment the arterial pressure signal is obtained from a noninvasive blood pressure measuring device.

In another preferred embodiment the duration of systole parameter involves a measurement of the time elapsed between the onset of systole and the peak arterial blood pressure.

In another preferred embodiment, the coefficients associated with the formula or algorithm are determined by analyzing a training set of arterial blood pressure signal data for which the associated stroke volumes have been independently measured.

EXAMPLE

Several experiments were carried out which further illustrate embodiments of the systems and methods described above. Details of the experiments are provided in the following examples.

Example

In this example, data from six Yorkshire Swine (30-34 kg) previously recorded under a protocol approved by the MIT Committee on Animal Care were processed and analyzed offline. During the actual trials with each swine, both aortic blood flow and femoral ABP were recorded using an ultrasonic flow probe (T206 with A-series probes, Transonic Systems, Ithaca, N.Y.) placed around the aortic root and an external pressure transducer (TSD104A, Biopac Systems, Santa Barbara, Calif.). For details of the data record and protocol following during the actual trials, refer to R. Mukkamala, et al., "Continuous cardiac output monitoring by peripheral blood pressure waveform analysis," *IEEE Trans Biomed Eng*, vol. 53, pp. 459-67, March 2006.

Algorithms based upon the methods described above were developed to process the swine data. The algorithms were applied to the swine data to calculate beat-to-beat $\tau_i$ estimates. The $\tau_i$ values were then used to estimate values for proportional TPR, CO and SV. These values could then be scaled and compared with reference values for TPR, CO and SV, which were determined from the recorded aortic blood flow data, i.e., the data obtained with the blood flow probe.

By analysis of femoral ABP, end-DBP, $P_i^D$, time interval $T_i$, duration of systole $T_i^S$, and $MAP_{i,r}$ were determined from ABP waveforms and applied to EQS. 9A-C to obtain a characteristic time constant $\tau_i$ for each cardiac cycle. For this example, the medians of $\tau_i$ and $T_i^S$ over a 20-second moving window were taken to exclude outliers, and regarded as the $\tau_i$ value of the beat. Other time intervals could be used of obtaining median values of $\tau_i$, e.g., up to about 5 seconds, up to about 10 seconds, up to about 40 seconds, up to about 60 seconds. The median $\tau_i$ values were applied to EQS. 4 and 7 to estimate proportional TPR, proportional CO and proportional SV on a beat-to-beat basis. In order to compare the CO estimation with the ARMA method, the beat-to-beat CO estimates were averages over six minutes.

$C_a$ of each swine was estimated to compare proportional TPR (i.e., characteristic time constant $\tau$ in EQ. 2) calculated by this new method with the measured reference values of TPR. As an example, in each swine data set, the mean of the estimated proportional TPR was divided by the mean value of the measured TPR to obtain a value for AC. Although AC declines with age, it is regarded as constant for a short period of time. The estimated proportional CO was then scaled by the AC value to yield an absolute TPR estimate. The error criterion $$\delta_n = \left| \frac{R_n - E_n}{R_n} \right| \quad (14a)$$

where $R_n$ is a measured reference value, and $E_n$ is an estimated value, was compared to those estimated by conventional pulse pressure methods. The preset algorithm achieved 14.0%, smaller error than the conventional pulse pressure methods.

For evaluation of CO and SV estimation, root normalized mean square log errors (RNMSLEs) of the absolute CO and SV estimates (normalized by the measured values and given in percent) were then calculated:

$$RNMSLE = 100 \sqrt{\frac{\sum_{n=1}^{N} (\ln(E_n) - \ln(R_n))^2}{N - n_f}} = 100 \sqrt{\frac{\sum_{n=1}^{N} \left( \ln\left(\frac{E_n}{R_n}\right) \right)^2}{N - N_f}} \quad (14b)$$

where N is the number of data and $N_f$ is the umber of free parameters. The logarithmic form of the error RNMSLE was adopted because the estimation procedure involves logarithm in the linearization step, from EQ. 10 to EQ. 11. The new method minimizes SV error in a logarithm scale:

$$(\ln(SV^{est}) - \ln(SV^{meas}))^2 = \left( \ln\left(\frac{SV^{est}}{SV^{meas}}\right) \right)^2 \quad (15)$$

rather than a normal form of error:

$$\left( \frac{SV^{est} - SV^{meas}}{SV^{meas}} \right)^2 \quad (16)$$

The difference of EQ. 15 and EQ. 16 are small when $SV^{est}$ and $SV^{meas}$ are close, because:

$$(\ln x)^2 \approx (x-1)^2 \text{ around } x = 1 \quad (17a)$$

$$\Rightarrow \left( \ln\left(\frac{SV^{est}}{SV^{meas}}\right) \right)^2 \approx \left( \frac{SV^{est}}{SV^{meas}} - 1 \right)^2 = \quad (17b)$$

$$\left( \frac{SV^{est} - SV^{meas}}{SV^{meas}} \right)^2 \text{ around } \frac{SV^{est}}{SV^{meas}} = 1$$

Absolute CO and SV estimates obtained by methods of the present invention were compared with values estimated by the ARMA technique (CO estimates only), traditional PP method (PP1), and Herd's PP method (PP2) (J. A. Herd, N. R. Leclair, and W. Simon, "Arterial pressure pulse contours during hemorrhage in anesthetized dogs," *J Application Physiol*, vol. 21, pp. 1864-8, November 1966) by F-test. Significance was set at p<00.5.

Table I summarizes the physiological ranges of the Yorkshire Swine data sets (94 minutes in average) and the estimation results using the new method. Using the MDL analysis, eighth order was selected for use of femoral arterial, and ninth order for use of radial arterial. Over the wide physiological range, the new method achieved 12.7% CO and 16.5% SV errors using femoral arterial, and 10.1% CO and 14.5% SV errors using radial ABP.

Even with the normal criteria EQ. 16, the new method had lower errors in CO (femoral: 10.4%, radial: 10.3%) and SV (femoral: 12.7%, radial: 12.7%) estimation than other methods.

Figure 6A:
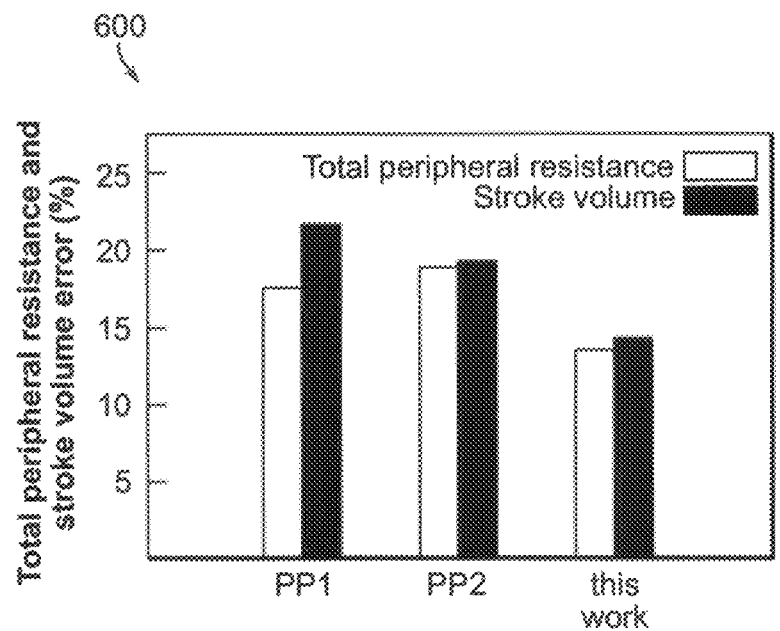
FIG. 6A depicts estimation errors for total peripheral resistance (empty bars) and stroke volume (solid bars) determined using the methods of the present teachings compared with conventional pulse pressure methods.
Figure 6B:
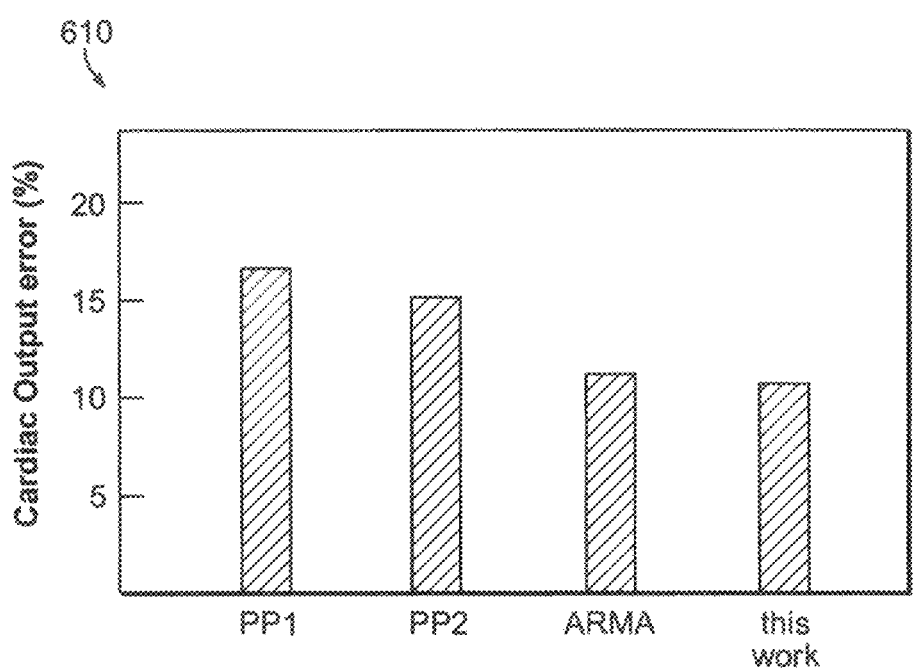
FIG. 6B depicts estimation error for cardiac output (CO) determined using the methods of the present teachings compared with conventional pulse pressure methods and an auto-regressive moving average (ARMA) method.

The overall trend of the measured and estimated CO and SV showed strong agreement (FIG. 5). Correlation coefficients between the aortic blood flow and the estimation from the "femoral ABP" were 0.893 (CO) and 0.836 (SV) and from the "radial ABP" were 0.941 (CO) and 0.826 (SV). Over 93% of the estimation errors were within two standard deviations. The new method had smaller RNMSLE (P<0.05) than the other methods in both CO and SV estimations (FIG. 6). The CO and SV estimation errors by the new method did not show apparent trend in accordance with MAP, which demonstrated reliability of the method over the wide MAP range. Note that MAP was calculated on a six-minute window basis for CO analysis and on a beat-to-beat basis for SV analysis resulting in the different scales displayed on the horizontal axes.

Table I

Summary of Cardiovascular Indices of the Five Swine Data Sets

TABLE I

SUMMARY OF CARDIOVASCULAR INDICES OF THE FIVE SWINE DATA SETS

| ANIMAL | Length (min) | CO (L/min) | SV (mL) | Femoral MAP (mmHg) | Radial MAP (mmHg) | HR (bpm) |
|---|---|---|---|---|---|---|
| 1 | 113 | 3.6 +/− 1.5 | 28.4 +/− 11.7 | 63 +/− 32 | 61 +/− 32 | 129 +/− 52 |
| 2 | 97 | 3.2 +/− 0.8 | 25.0 +/− 9.0 | 83 +/− 38 | 73 +/− 37 | 139 +/− 64 |
| 3 | 88 | 4.0 +/− 1.1 | 31.7 +/− 12.6 | 83 +/− 28 | 87 +/− 28 | 133 +/− 48 |
| 4 | 106 | 3.2 +/− 0.9 | 25.2 +/− 1.1 | 89 +/− 30 | 79 +/− 30 | 129 +/− 62 |
| 5 | 90 | 3.3 +/− 0.7 | 26.7 +/− 12.0 | 80 +/− 34 | 85 +/− 31 | 130 +/− 50 |
| 6 | 68 | 3.4 +/− 2.1 | 28.5 +/− 17.1 | 72 +/− 34 | 75 +/− 35 | 130 +/− 40 |
| TOTAL | 562 | 3.5 +/− 1.7 | 27.5 +/− 13.4 | 79 +/− 37 | 76 +/− 38 | 131 +/− 58 |

The wide physiological ranges (mean+/−95% confidence interval) of cardiac output (CO), stroke volume (SV), femoral and radial [mean?] arterial blood pressure (MAP), and heart rate (HR) were covered in the six swine data sets. The four columns on the right show the results of CO and SV estimation by the new method using femoral and radial ABP.

All literature and similar material cited in this application, including, but not limited to, patents, patent applications, articles, books, treatises, and web pages, regardless of the format of such literature and similar materials, are expressly incorporated by reference in their entirely. In the event that one or more of the incorporated literature and similar materials differs from or contradicts this application, including but not limited to defined terms, term usages, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The claims should not be read as limited to the described order or elements unless states to that effect. It should be understood that various changes in form ad detail may be made by one of ordinary skill in the art without departing from the spirit and scope of the appended claims. All embodiments that come within the spirit and scope of the following claims and equivalents thereto are claimed.

REFERENCES

1. A. C. Guy and J. E. Hall, *Textbook of Medical Physiology*, $10^{th}$ ed. Philadelphia: Saunders 2000.
2. H. Barcroft, O. G. Edholm, J. McMichael, and E. P. Sharpy-Schafer, "Posthaemorrhagic fainting. Study by cardiac output and forearm flow," *Lancet*, pp. 489-491, 1944.
3. R. Mukkamala, A. T. Reisner, H. M. Hojrnans, R. G. Mark, and R. J. Cohen, "Continuous cardiac output monitoring by peripheral blood pressure waveform analysis," *IEEE Transportation Biomed Eng*, vol. 53, pp. 459-67, Market 2006.
4. W. Ganz, R. Donoso, H. S. Marcus, J. S. Forrester, and H. J. Swan, "A new technique for measurement of cardiac output by thermodilution in man," *Am J Cardiol*, vol. 27, pp. 392-6, April 1971.
5. R. D. Yoder and E. A. Swan, "Cardiac output; comparison of Stewart-Hamilton and gamma-function techniques," *J Appl Physiol*, vol. 31, pp. 318-21, August 1971.
6. R. J. Levy, R. M. Chiavacci, S. C. Nicolson, J. J. Rom, R. J. Lin, M. A. Helfaer, and V. M. Nadkami, "An evaluation of a noninvasive cardiac output measurement using partial carbon dioxide rebreathing in children," *Anesth Analg*, vol. 99, pp. 1642-7, table of contents, Decision 2004.
7. M. Botero, D. Kirby, E. B. Lobato, E. D. Staples, and N. Gravenstein, "Measurement of cardiac output before and after cardiopulmonary bypass: Comparison among aortic transit-time ultrasound thermodilution, and noninvasive partial CO2 rebreathing," *J Cardiothorac Vasc Anesth*, vol. 18, pp. 563-72, October 2004.
8. M. J. Bourgeois, B. K. Gilbert, G. Von Bemuth, and E. H. Wood, "Continuous determination of beat to beat stroke volume from aortic pressure pulses in the dog," *Circ Res*, vol. 39, pp. 15-24, July 1976.
9. G. Antonutto, M. Girardis, D. Tuniz, and P. E. di Prampero, "Noninvasive assessment of cardiac output from arterial pressure profiles during exercise," *Eur J Appl Physiol Occup Physiol*, vol. 72. pp. 18-24, 1995.

10. J. D. Redling and M. Akay, "Noninvasive cardiac output estimation: a preliminary study," *Biol Cybern*, vol. 77, pp. 111-22, August 1997.

11. T. Nieminen, T. Koobi, and V. Turjanmas, "Can stroke volume and cardiac output be determined reliably in a tilt-table test using the pulse contour method?" *Clin Physiol*, vol. 20, pp. 488-95, November 2000.

12. C. Cerutti, M. P. Gustin, P. Molino, and C. Z. Paultre, "Beat-to-beat stroke volume estimation from aortic pressure waveform in conscious rats: comparison of models, *Am J Physiol Heart Cir Physiol*, vol. 281, pp. HI 148-55, September 2001.

13. N. W. Linton and R. A. Linton, "Estimation of changes in cardiac output from the arterial blood pressure waveform in the upper limb," *Br J Anaesth*, vol. 86, pp. 486-96, April 2001.

14. G. Antonutto. M. Girardis, M. Tuniz, E. Petri, and C. Capelli, "Assessment of cardiac output from noninvasive determination of arterial pressure profile in subjects at rest," *Eur J Appl Physiol Occup Physiol*, vol. 69, pp. 183-8, 1994.

15. W. J. Stok. R. C. Stringer, and J. M. Karemaker, "Noninvasive cardiac output measurement in orthostasis: pulse contour analysis compared with acetylene rebreathing," *J Appl Physiol*, vol. 87, pp. 2266-73, December 1999.

16. J. I. van Lieshout and K. H. Wesseling, "Continuous cardiac output by pulse contour analysis?" *Br J Anaesth*, vol. 86, pp. 467-9, April 2001.

17. D. Burkhoff, J. Alexruider. Jr., and I. Schipke. "Assessment of Windkessel as a model of aortic input impedance," *Am J Physiol*, vol. 255, pp. H742-53, October 1988.

18. Z. Lu and R. Mukkamala, "Continuous cardiac output monitoring in humans by invasive and noninvasive peripheral blood pressure waveform analysis," *J Appl Physiol*, vol. 101, pp. 598-608, August 2006.

19. P. Molini, C. Cerutti, C. Julien, G. Cuisinaud, M. P. Gustin, and C. Paultre, "Beat-to-beat estimation of Windkessel model parameters in conscious rats," *Am J Physiol*, vol. 274, pp. H171-7, January 1998.

20. J. A. Herd, N. R. Leclair, and W. Simon, "Arterial pressure pulse contours during hemorrhage in anesthetized dogs," *J Appl Physiol*, vol. 21, pp. 1864-8, November 1966.

21. M. W. Mohiuddin, G. A. Leine, and C. M. Quick, "Increase in pulse wavelength causes the systemic arterial tree to degenerates into a classical Windkessel," *Am J Appl Physiol Cir Physiol*, vol. 293, pp. HI 164-71, August 2007.

22. J. M. Bland and D. G. Altman, "Statistical methods for assessing agreement between two methods of clinical measurement," *Lancet*, vol. I, pp. 307-10, Feb. 8, 1986.

23. K. Dewitte, C. Fierens, D. Stocki, and L. M. Thienpont, "Application of the Bland-Altman plot for interpretation of method-comparison studies: a critical investigation of its practice," *Clin Chem*, vol. 48, pp. 799-801: author reply 801-2, May 2002.

24. X. Xiao, S. M. Grenon, C. Kim, N. Sheynberg, S. Hurwitz, O. H. Williams, and R. J. Cohen. "Bed restaurant effects on human calf hemodynamics and orthostatic intolerance: a model-based analysis," *Aviat Space Environ Med*, v. 76, pp. 1037-45, November 2005.

25. H. Weaseling. B. De Werr, J. A. P. Weber, and N. T. Smith, "A simple device for the continuous measurement of cardiac output. Its model basis and experimental verification," *Adv Cardiovasc Phys*, vol. 5, pp. I 6-52, 1983.

26. K. H. Weseling, J. R. Januen, J. J. Settels, and J. J. Schreuder, "Computation of aortic flow from pressure in humans using a nonlinear, three-dimensional model," *J Appl Physiol*, vol. 74, pp. 2566-73, May 1993.

27. J. Sugawara, T. Tanabe, M. Miyachi, K. Yamamoto, K. Takahashi, M. Iemitsu, T. Otsuki, S. Homms, S. Macda, R. Ajisaka, and M. Matsuda, "Non-invasive assessment of cardiac output during exercise in healthy young humans: comparison between Modelflow method and Doppler echocardiography method," *Acta Physiol Scand*, vol. 179, pp. 361-6, Decision 2003.

28. E. Tam, M. Azabji Kenfack, M. Cautero, F. Lador, G. Antonutto, P. E. di Prampero, G. Farretti, and C. Capelli, "Correction of cardiac output obtained by Modeflow from finger pulse pressure profiles with a respiratory method in humans," *Clin Sci (Lond)*, vol. 106, pp. 371-6, April 2004.

29. J. J. Remmen, W. R. Aengevaeren, F. W. Verheugt, T. van ver Werf, H. E. Luijten, A. Boston, and R. W. Jansen, "Finapres arterial pulse wave analysis with Modelflow is not a reliable non-invasive method for assessment of cardiac output," *Clin Sci (Lond)*, vol. 103, pp. 143-9, August 2002.

30. T. Nakamura, K. Meguro, K. Huae, S. Ono, S. Matsushita, and T. Ozawa, "[Evaluation of continuous blood pressure monitoring by arterial tonometry in the aged]," *Masui*, vol. 46, pp. 1618-24, December 1997.

31. R. A. Nelesen and J. E. Dimsdale, "Use of radial arterial tonometric continuous blood pressure measurement in cardiovascular reactivity studies," *Blood Press Monit*, vol. 7, pp. 259-63, October 2002.

The invention claimed is:

1. A method performed on a computer for estimating stroke volume of a cardiac cycle of a heart comprising:
   a. recording an arterial blood pressure signal;
   b. processing with the computer the arterial blood pressure signal to obtain five parameters which are insensitive to distortions resulting from propagation of an arterial pulse through an arterial tree; the five parameters consisting of mean arterial pressure of a cardiac cycle, end-diastolic pressure of the cardiac cycle, end-diastolic pressure of an immediately preceding cardiac cycle, duration of the cardiac cycle and duration of systole of the cardiac cycle;
   c. incorporating only the five parameters into a formula or algorithm to estimate with the computer the stroke volume of the cardiac cycle of the heart;
   d. estimating with the computer the stroke volume from the formula or algorithm; and
   e. outputting the estimated stroke volume from the computer and
   f. wherein the method further comprises estimating a characteristic time constant of the cardiac cycle and the method further includes determining coefficients associated with the formula or algorithm by analyzing a training set of arterial blood pressure signal data for which the associated stroke volumes have been independently measured.

2. Method of estimating the stroke volumes of a plurality of cardiac cycles of the heart comprising applying the method of claim 1 to multiple cardiac cycles of the heart.

3. Method of claim 1 wherein the formula or algorithm incorporates a model.

4. Method of claim 3 wherein the model is a Windkessel-type model.

5. Method of claim 3 wherein the formula or algorithm incorporates one or more means of fitting the arterial blood pressure signal to one or more models.

6. Method of claim 5 wherein the formula or algorithm incorporates one or more means of fitting the arterial blood pressure signal to a Windkessel-type model.

7. Method of claim 1 wherein the formula or algorithm utilizes a number of dimensionless parameters.

8. Method of claim 1 wherein the time constant associated with the cardiac cycle is estimated from time constants estimated for a plurality of cardiac cycles preceding and/or following the cardiac cycle.

9. Method of claim 2 further comprising estimating cardiac output.

10. Method of claim 2 further comprising estimating total peripheral vascular resistance.

11. Method of claim 1 wherein the recording step obtains the arterial blood pressure signal from an intra-arterial measurement location.

12. Method of claim 1 wherein the recording step obtains the arterial blood pressure signal from a noninvasive blood pressure measuring device.

13. Method of claim 1 further including measuring the time elapsed between onset of systole and the peak arterial blood pressure to provide the duration of systole.

14. Method of claim 1 further including determining coefficients associated with the formula or algorithm by analyzing a training set of arterial blood pressure signal data for which an associated stroke volumes have been independently measured.

15. A system for estimating stroke volume of a cardiac cycle of a heart comprising:
   a. recording means for recording an arterial blood pressure signal;
   b. computer means configured for processing the arterial blood pressure signal to obtain five parameters which are insensitive to distortions resulting from the propagation of an arterial pulse through an arterial tree, the five parameters consisting of mean arterial pressure of the cardiac cycle, end-diastolic pressure of the cardiac cycle, end-diastolic pressure of an immediately preceding cardiac cycle, duration of the cardiac cycle, and duration of systole of the cardiac cycle; and
   c. the computer means also configured for incorporating only the five parameters into a formula or algorithm to estimate the stroke volume of the cardiac cycle of the heart;
   d. the computer means also configured for estimating stroke volume from the formula or algorithm; and
   e. a display for outputting stroke volume and
   f. wherein the computer means is also configured to (i) estimate a characteristic time constant of the cardiac cycle and (ii) determine coefficients associated with the formula or algorithm by analyzing a training set of arterial blood pressure signal data for which the associated stroke volumes have been independently measured.

16. The system of claim 15 wherein the computer means is adapted to estimating the stroke volume from a plurality of cardiac cycles of the heart.

17. The system of claim 15 wherein the formula or algorithm incorporates a model.

18. The system of claim 17 wherein the model is a Windkessel-type model.

19. The system of claim 17 wherein the formula or algorithm incorporates one or more means of fitting the arterial blood pressure signal to one or more models.

20. The system of claim 19 wherein the formula or algorithm incorporates one or more means of fitting the arterial blood pressure signal to a Windkessel-type model.

21. The system of claim 15 wherein the formula or algorithm utilizes a number of dimensionless parameters.

22. The system of claim 15 wherein the time constant associated with the cardiac cycle is estimated from time constants estimated for a plurality of cardiac cycles preceding and/or following the cardiac cycle.

23. The system of claim 16 further comprising means for estimating cardiac output.

24. The system of claim 16 further comprising means for estimating total peripheral vascular resistance.

25. The system of claim 15 wherein the recording means is configured to obtain the arterial blood pressure signal from an intra-arterial measurement location.

26. The system of claim 15 wherein the recording means is configured to obtain the arterial blood pressure signal from a non-invasive blood pressure measuring device.

27. The system of claim 15 further including means for measuring time elapsed between onset of systole and peak arterial blood pressure to provide duration of systole.

* * * * *

UNITED STATES PATENT AND TRADEMARK OFFICE
CERTIFICATE OF CORRECTION

| | |
|---|---|
| PATENT NO. | : 9,560,977 B2 |
| APPLICATION NO. | : 14/315741 |
| DATED | : February 7, 2017 |
| INVENTOR(S) | : Cohen et al. |

Page 1 of 1

It is certified that error appears in the above-identified patent and that said Letters Patent is hereby corrected as shown below:

In the Specification

In Column 1, after Line 9, insert heading & paragraph:
--GOVERNMENT SUPPORT
This invention was made with government support under IIS0515869 awarded by the National Science Foundation. The government has certain rights in the invention.--

Signed and Sealed this
Eighteenth Day of November, 2025

John A. Squires
*Director of the United States Patent and Trademark Office*